US007763046B2

(12) United States Patent
Schouten et al.

(10) Patent No.: US 7,763,046 B2
(45) Date of Patent: Jul. 27, 2010

(54) BAND WITH SELECTIVELY ADJUSTABLE PRESSURE ORB

(75) Inventors: Pieter Schouten, Berkeley, CA (US); Carla Falcone, Sammamish, WA (US); Romy Taormina, Pacific Grove, CA (US)

(73) Assignee: PSI Health Solutions, Inc., Berkeley, CA (US)

(*) Notice: Subject to any disclaimer, the term of this patent is extended or adjusted under 35 U.S.C. 154(b) by 1009 days.

(21) Appl. No.: 11/464,354

(22) Filed: Aug. 14, 2006

(65) Prior Publication Data

US 2007/0198055 A1 Aug. 23, 2007

Related U.S. Application Data

(60) Provisional application No. 60/595,951, filed on Aug. 19, 2005.

(51) Int. Cl.
*A61B 17/00* (2006.01)

(52) U.S. Cl. .................................................... 606/204

(58) Field of Classification Search ................. 606/204; 601/97, 107, 135

See application file for complete search history.

(56) References Cited

U.S. PATENT DOCUMENTS

| | | | | |
|---|---|---|---|---|
| 1,481,354 | A | 1/1924 | Dingfeld | |
| 2,073,289 | A | 3/1937 | Shaw | |
| 4,308,861 | A * | 1/1982 | Kelly | 606/204 |
| 4,479,495 | A * | 10/1984 | Isaacson | 606/204 |
| 5,078,728 | A * | 1/1992 | Giarratano | 606/204 |
| 5,295,996 | A * | 3/1994 | Blair | 606/203 |
| 5,470,304 | A | 11/1995 | Decanto | |
| 5,695,520 | A * | 12/1997 | Bruckner et al. | 606/204 |
| 2004/0098037 | A1 * | 5/2004 | Grey et al. | 606/204 |
| 2005/0049631 | A1 * | 3/2005 | Carter-Smith et al. | 606/204 |

* cited by examiner

*Primary Examiner*—Todd E Manahan
*Assistant Examiner*—Naquan Ishman
(74) *Attorney, Agent, or Firm*—George R. McGuire; bond Schoeneck & King, PLLC

(57) ABSTRACT

The present invention provides a device for applying pressure to a wearer of the device, that includes a band adapted for positioning on the wearer, an orb positioned on the band, and a mechanism for selectively varying the length that the orb extends outward from said band. The mechanism includes a dial that is mounted to the orb for user initiated selective rotation about its central axis. By rotating the dial, the orb moves towards or away from the band, thereby decreasing or increasing, respectively, the amount of pressure it will apply to the wearer.

14 Claims, 6 Drawing Sheets

BAND WITH SELECTIVELY ADJUSTABLE PRESSURE ORB

PRIORITY CLAIM

The present application claims priority to U.S. Provisional Application Ser. No. 60/595,951, filed Aug. 19, 2005, the entirety of which is hereby incorporated by reference.

BACKGROUND OF THE INVENTION

The present invention relates generally to pressure orbs, and more particularly to pressure orbs worn on a person's wrist.

Pressure orbs are used for applying pressure to a person's pressure points to alleviate stress, nausea, headaches and other ailments known to be alleviated through application of pressure to a particular part of the body. In their most form, pressure orbs comprises a dome shaped orb that extends inwardly from a band that is worn by a user. The pressure orb is positioned over a pressure point and the band is either pre-sized or adjustable by the wearer such that the orb presses on the pressure point with a desired amount of pressure.

While pressure orbs are generally thought at being effective for their intended purpose of alleviating a psychological or physiological ailment, they are not always fashionable to wear, and depending on the amount of pressure desired, multiple orbs may need to be owned and used when appropriate.

It is a principal object and advantage of the present invention to provide a pressure orb that is selectively adjustable in the amount of pressure it will apply to a wearer.

It is another object and advantage of the present invention to incorporate an adjustable pressure orb into a fashionable band which may optionally be combined with another article, such as a watch.

It is a further object and advantage of the present invention to provide a pressure orb that is selectively adjustable at the pressure point.

It is yet another object and advantage of the present invention to provide two independent pressure adjustment mechanisms in a band.

Other objects and advantages of the present invention will in part be obvious, and in part appear hereinafter.

SUMMARY OF THE INVENTION

In accordance with the foregoing objects and advantages, the present invention provides a device for applying pressure to a wearer of the device, comprising a band adapted for positioning on the wearer; an orb positioned on the band; and a mechanism for selectively varying the length that the orb extends outward from said band.

In a preferred embodiment, the adjustment mechanism comprises a dome shaped nut positioned within and in movable relation to the orb; a ring positioned circumferentially within the orb, a tube extending outwardly from the dome shaped nut and about a longitudinal axis, and first and second slots connected to opposing sides of the tube and extending transverse to the ring; first and second wings formed on the dome shaped nut that are adapted for sliding movement within the first and second slots, respectively; a dial positioned in contacting relation to the dome shaped nut for rotational movement about the longitudinal axis; first and second stepped ramps concentrically arranged on and extending downwardly from the dial and having a series of notches defined therein between successive steps, wherein the first and second stepped ramps are adapted for engagement with the first and second wings, respectively, and are also adapted for secure positioning within the notches formed in the first and second stepped ramps.

BRIEF DESCRIPTION OF THE DRAWINGS

The present invention will be more fully understood and appreciated by reading the following Description in conjunction with the accompanying drawings, in which.

DETAILED DESCRIPTION

Figure 2:
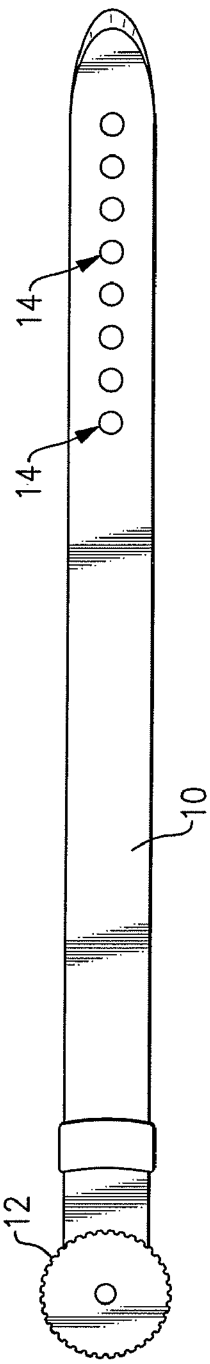
FIG. 2 is a top plan view thereof.
Figure 1:
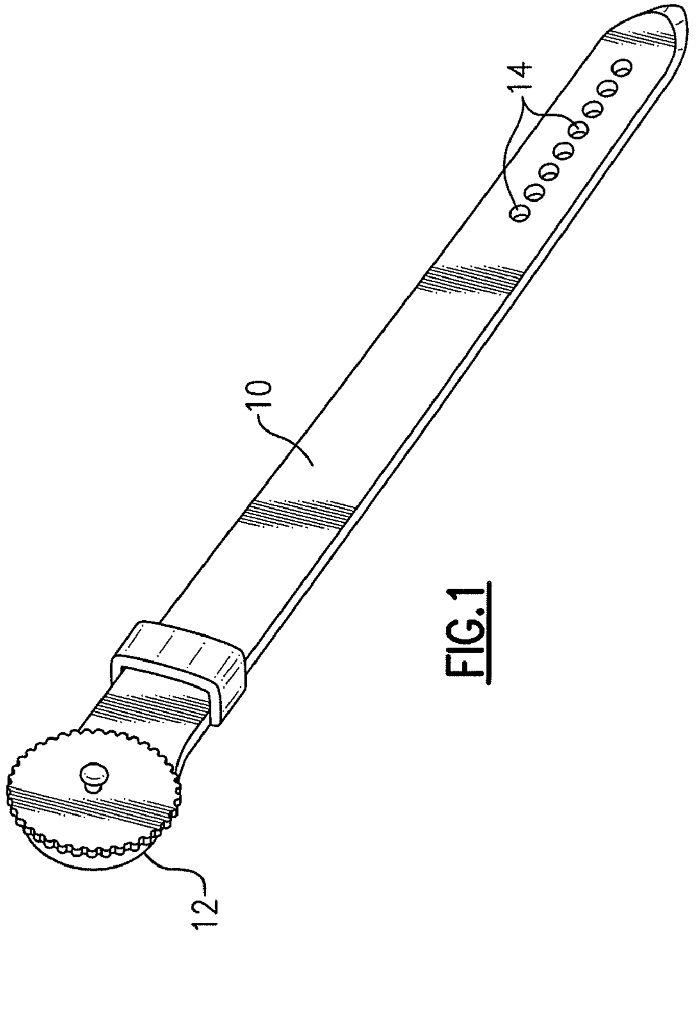
FIG. 1 is a perspective view of a pressure orb band.
Figure 3A:
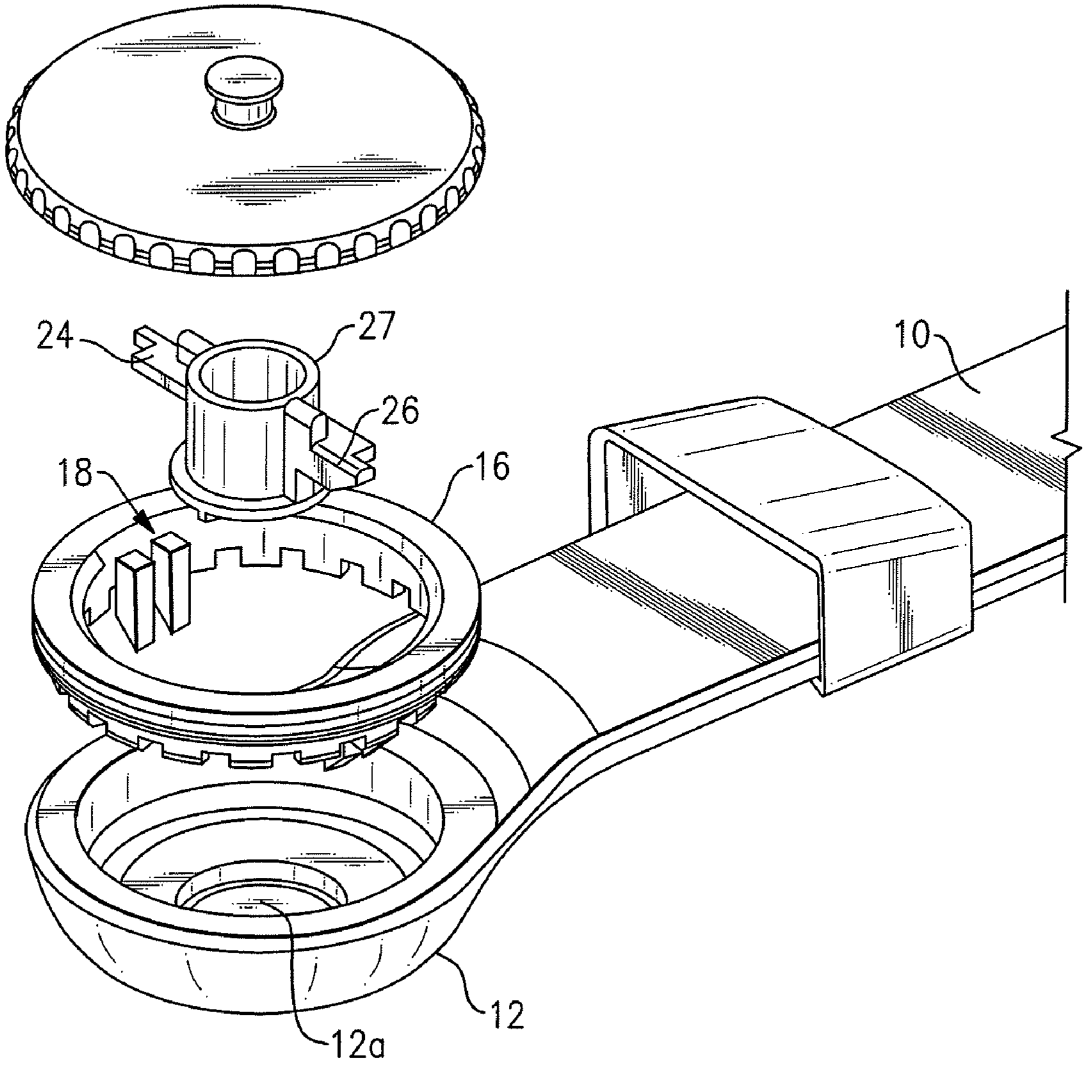
FIGS. 3A and 3B are exploded perspective views of the orb end of the band and the pressure adjusting mechanisms with the ring shown outside and insert molded within the orb, respectively.
Figure 3B:
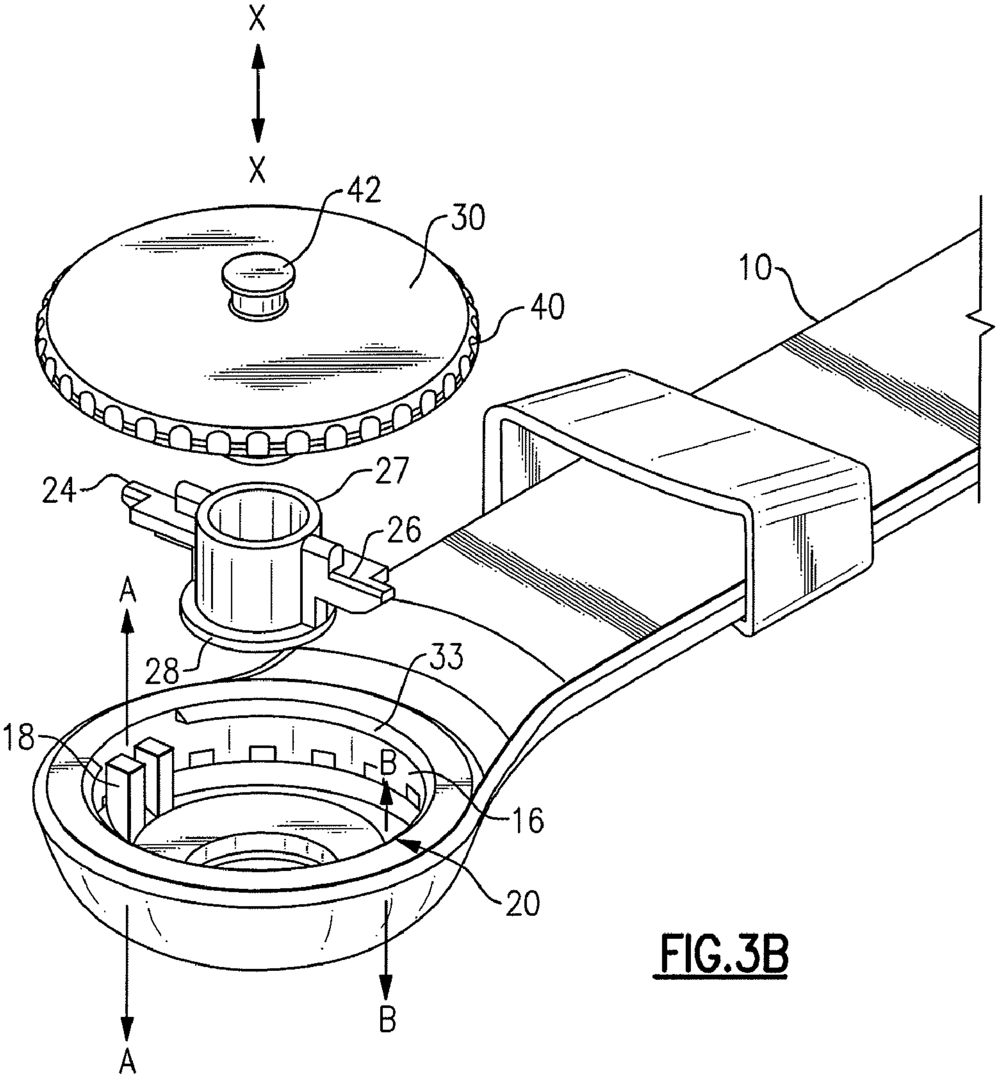
Figure 4A:
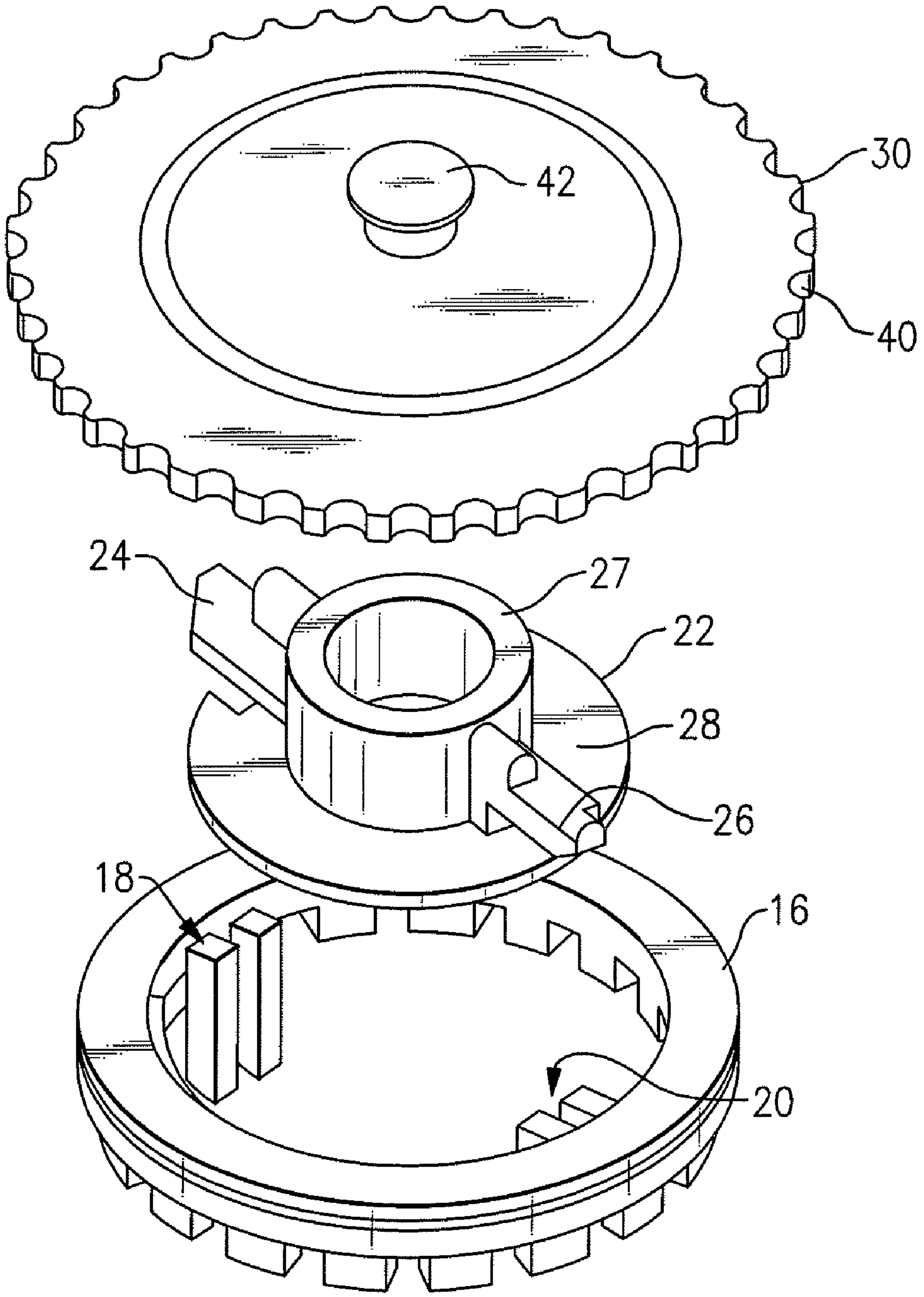
FIGS. 4A and 4B are exploded perspective views of the pressure adjustment mechanisms for the orb.
Figure 4B:
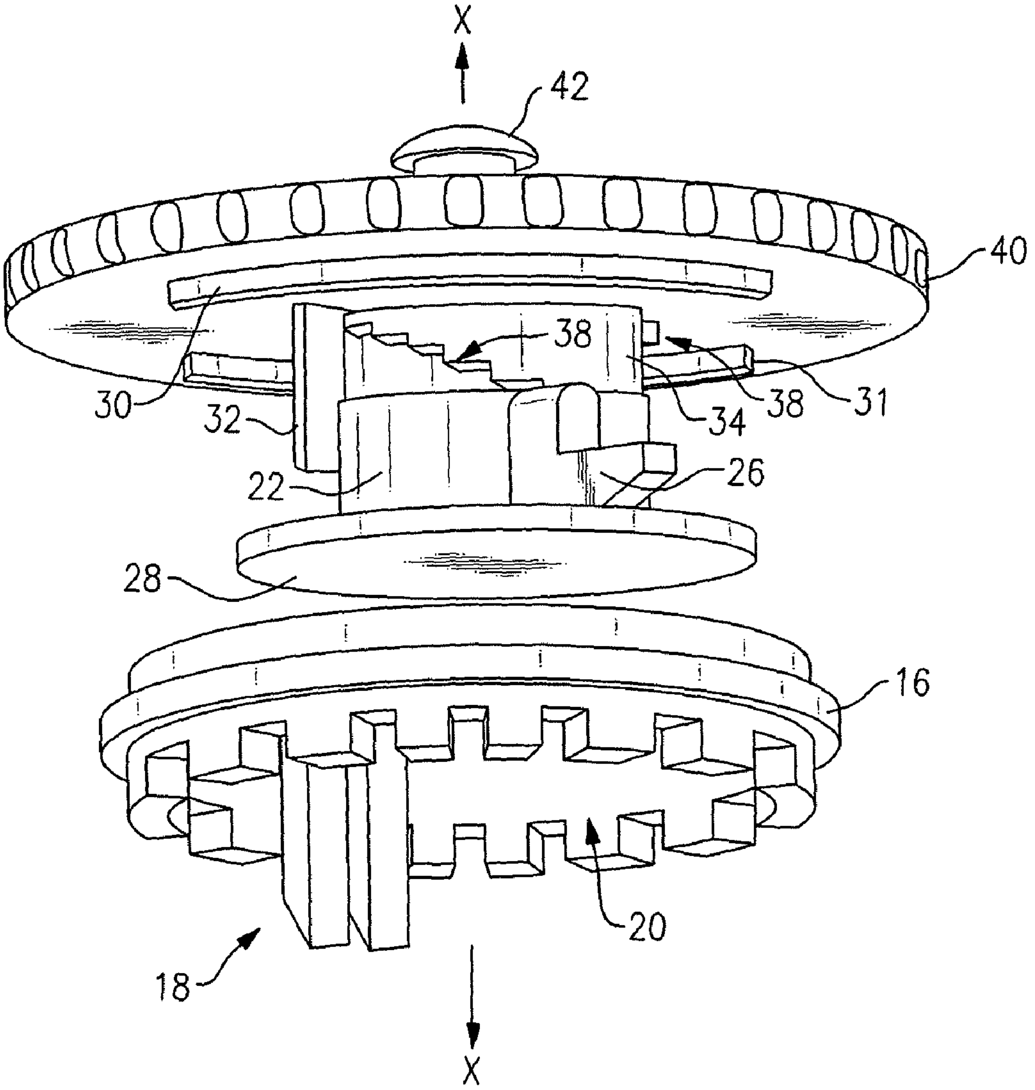
Figure 5:
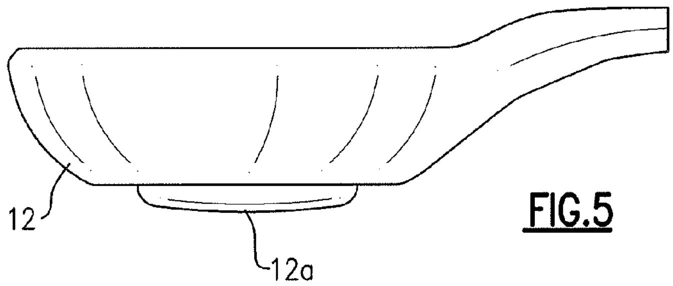
FIG. 5 is a side elevation view of the orb end of the band showing an alternate embodiment of the orb.
Figure 6:
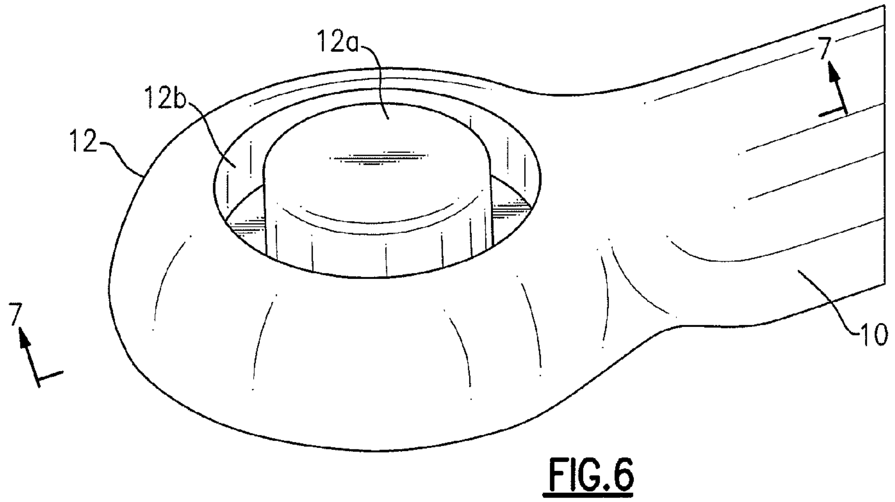
FIG. 6 is a perspective view of the orb of FIG. 5.
Figure 7:
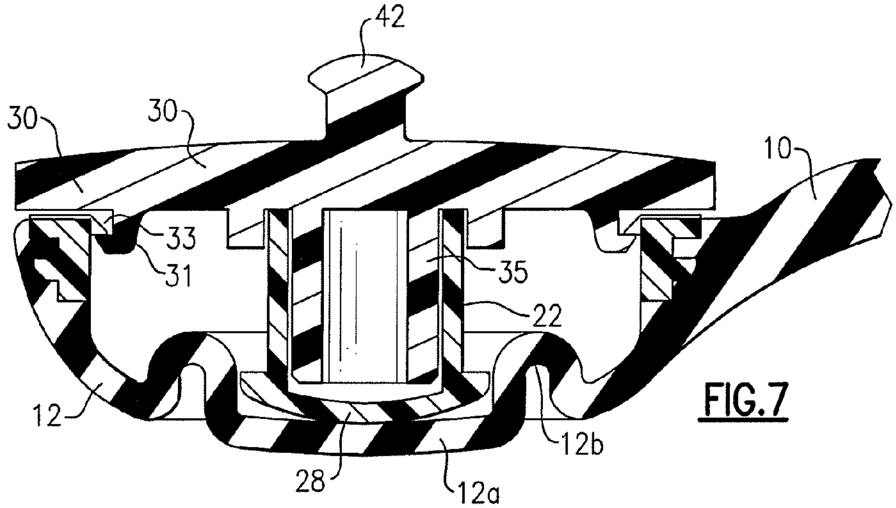
FIG. 7 is a cross-sectional view of the orb end of the band taken along section line 7-7 of FIG. 6.

Referring now to the drawings, wherein like reference numerals refer to like parts throughout, there is seen in FIG. 1 an elastomeric band, designated generally by reference numeral 10, that includes a hollow, hemi-spherical pressure orb 12 incorporated at a first end thereof. In one embodiment as illustrated in FIGS. 5-7, orb 12 can include a pressure point contacting region 12*a* that is adapted to contact and apply pressure to a wearer's pressure point, such as the P6 pressure point located on a person's wrist. Region 12*a* is defined by a bellow 12*b* formed around the region that facilitates the resilient inward and outward movement of the region. Band 10 is elongated and includes a plurality of longitudinally spaced apart openings 14 formed therethrough that extend from a second end of the band. Each opening 14 permits band 10 to be fastened around a wearer's wrist at a desired circumference.

The interior of orb 12 is hollow and includes a ring 16 positioned therein (preferably insert molded into orb 12). Ring 16 includes a pair of diametrically opposed slots 18, 20 formed therein that extend along parallel axes A-A and B-B that are essentially perpendicular to the plane in which the open top surface of orb 12 lies. The upper surface of ring 16 extends co-planar with the open, upper end of orb 12.

A nut 22 is movably positioned within orb 12. Nut 22 includes a pair of opposed wings 24, 26 that extend outwardly from diametrically opposite sides of a central tube 27 and are positioned within slots 18, 20, respectively, for sliding movement along axes A-A and B-B and. The walls that define channels 18 and 20 prevent rotational movement of nut 22. The bottom end of nut 22 includes an essentially dome shaped disc 28 that is positioned in contacting relation to the interior surface of pressure point contacting region 12*a* of orb 12 and presses the orb outwardly (or permits it to retreat inwardly), as will be described hereinafter.

A dial 30 is movably positioned in contacting relation to nut 22, and is secured in relation to nut 22 by a resilient flange 31 that engages the underside of a flange 33 formed about the periphery of ring 16 and a central post 35 that sits within tube 27, thereby fixing the position of dial 30 and preventing it from becoming inadvertently separated from band 10. More particularly, dial 30 includes a pair of concentrically arranged, symmetrical, stepped ramps 32, 34 extending downwardly from the dial's bottom surface and which engage wings 24, 26, respectively. Each ramp 32, 34 includes a series of concave steps 36 that conclude in notches 38. Dial 30 is rotatable about its central axis X-X which is parallel to axes A-A and B-B, and as a wearer rotates dial 30 about its central axis, steps 36 press down on wings 24, 26 (causing nut 18 to slide longitudinally within orb 12) until the wings come to rest in the selected notch 38. As each notch 38 is positioned at a different relative distance from the plane in which the open top end of orb 12 extends than the other notches 38, the amount nut 22 is pressed inwardly into orb 12 selectively changes based upon the amount dial 30 has been rotated. As orb 12 (and region 12*a*) is composed of a flexible material, i.e., the same elastomeric material as band 10, orb 12 will expand outwardly or inwardly according to the amount of pressure exerted by the dome shaped disc 28.

Dial 30 further includes a side edge 40 that is notched to permit a wearer's finger to effectively grip and rotate the disc, thereby increasing or decreasing the amount of pressure exerted by orb 12, and a centrally positioned post 42 extending perpendicularly outward from its upper surface. Post 42 is adapted to have one of the openings 18 formed through band 10 passed thereover to close band 10 around a wearer's wrist. A wearer can further selectively increase or decrease the amount of pressure exerted by orb 12 by selecting an opening 18 that will create as tight or loose a fit as desired. Thus, a wearer has two pressure adjustment mechanisms that are both positioned at the pressure point (the openings 18 that are anchored by post 42 which extends from dial 30, and dial 30 itself that is selectively rotatable to increase or decrease the amount of pressure applied by orb 12).

What is claimed is:

1. A device for applying pressure to a wearer of the device, comprising:

a. a band adapted for positioning on the wearer;

b. an orb positioned on said band; and c. a first mechanism for selectively varying the length that said orb extends outward from said band, wherein said first mechanism comprises:

a dome shaped nut positioned within and in movable relation to said orb;

a ring positioned circumferentially within said orb;

a tube element extending about a longitudinal axis; and first and second slots connected to opposing sides of said tube element and extending transverse to said ring.

2. The device according to claim 1, wherein said first mechanism further comprises first and second wings formed on said dome shaped nut that are adapted for sliding movement within said first and second slots, respectively.

3. The device according to claim 2, wherein said first mechanism further comprises a dial positioned in contacting relation to said dome shaped nut for rotational movement about said longitudinal axis.

4. The device according to claim 3, wherein said first mechanism further comprises first and second stepped ramps concentrically arranged on and extending downwardly from said dial and having a series of notches defined therein between successive steps.

5. The device according to claim 4, wherein said first and second stepped ramps are adapted for engagement with said first and second wings, respectively, wherein said first and second ramps are adapted for secure positioning within said notches formed in said first and second stepped ramps.

6. The device according to claim 1, wherein sad band includes a plurality of openings formed therethrough.

7. The device according to claim 6, further comprising a dial attached to said orb for rotational movement about a central axis, wherein said dial includes a post extending outwardly therefrom, said post adapted for engagement with any one of said plurality of openings.

8. A device adapted for donning by a wearer to provide pressure to a predetermined point on the wearer, comprising:

a. a band with a fastening element adapted for positioning on the wearer;

b. a pressure orb mounted on said band for selective movement relative to said band; and c. means for selectively moving said pressure orb relative to said band, wherein said means for selectively moving said pressure orb relative to said band comprises:

a dome shaped nut positioned within and in movable relation to said orb;

a ring positioned circumferentially within said orb;

a tube element extending and about a longitudinal axis; and first and second slots connected to opposing sides of said tube element and extending transverse to said ring.

9. The device according to claim 8, wherein said means for selectively moving said pressure orb relative to said band, further comprises first and second wings formed on said dome shaped nut that are adapted for sliding movement within said first and second slots, respectively.

10. The device according to claim 9, wherein said means for selectively moving said pressure orb relative to said band, further comprises a dial positioned in contacting relation to said dome shaped nut for rotational movement about said longitudinal axis.

11. The device according to claim 10, wherein said means for selectively moving said pressure orb relative to said band, further comprises first and second stepped ramps concentrically arranged on and extending downwardly from said dial and having a series of notches defined therein between successive steps.

12. The device according to claim 11, wherein said means for selectively moving said pressure orb relative to said band, wherein said first and second stepped ramps are adapted for engagement with said first and second wings, respectively, wherein said first and second ramps are adapted for secure positioning within said notches formed in said first and second stepped ramps.

13. The device according to claim 8, wherein sad band includes a plurality of openings formed therethrough.

14. The device according to claim 13, further comprising a dial attached to said orb for rotational movement about a central axis, wherein said dial includes a post extending outwardly therefrom, said post adapted for engagement with any one of said plurality of openings.

* * * * *